United States Patent
Dunham et al.

(10) Patent No.: US 9,521,735 B2
(45) Date of Patent: Dec. 13, 2016

(54) PORTABLE X-RAY ANALYZER HAVING VIBRATION, THERMAL AND/OR MOISTURE ISOLATION FROM EXTERIOR ENVIRONMENT

(71) Applicant: X-RAY OPTICAL SYSTEMS, INC., East Greenbush, NY (US)

(72) Inventors: Daniel Dunham, Averill Park, NY (US); Rory D. Delaney, Slingerlands, NY (US)

(73) Assignee: X-RAY OPTICAL SYSTEMS, INC., East Greenbush, NY (US)

( * ) Notice: Subject to any disclaimer, the term of this patent is extended or adjusted under 35 U.S.C. 154(b) by 0 days.

(21) Appl. No.: 14/381,042

(22) PCT Filed: Feb. 27, 2013

(86) PCT No.: PCT/US2013/027918
§ 371 (c)(1),
(2) Date: Aug. 26, 2014

(87) PCT Pub. No.: WO2013/130531
PCT Pub. Date: Sep. 6, 2013

(65) Prior Publication Data
US 2015/0036804 A1    Feb. 5, 2015

Related U.S. Application Data

(60) Provisional application No. 61/604,933, filed on Feb. 29, 2012.

(51) Int. Cl.
*H01J 35/10*    (2006.01)
*H05G 1/02*    (2006.01)
(Continued)

(52) U.S. Cl.
CPC ............ *H05G 1/025* (2013.01); *G01N 23/223* (2013.01); *H05G 1/06* (2013.01); *G01N 2223/076* (2013.01)

(58) Field of Classification Search
CPC ............ H05G 1/04; H05G 1/025; H05G 1/06; G01N 23/223; G01N 2223/076
(Continued)

(56) References Cited

U.S. PATENT DOCUMENTS

| 7,020,238 B1 | 3/2006 | Kantonen et al. |
| 2006/0029185 A1 | 2/2006 | Baur et al. |

(Continued)

FOREIGN PATENT DOCUMENTS

JP    11224628 A    8/1999

OTHER PUBLICATIONS

International Search Report for PCT/US2013/027918 dated Jun. 20, 2013.

*Primary Examiner* — Coourtney Thomas
(74) *Attorney, Agent, or Firm* — Jeffrey Klembczyk, Esq.; Kevin P. Radigan, Esq.; Heslin Rothenberg Farley & Mesiti P.C.

(57) ABSTRACT

A handheld x-ray analyzer, having an outer shell forming an inner cavity, the outer shell having at least one aperture; an x-ray engine positioned within the cavity; and a generally planar heat sink rigidly and thermally attached to the x-ray engine, and positioned in the aperture of the outer shell thereby substantially filling the aperture while providing thermal conduction between the engine and surrounding air. An outer face of the heat sink may be substantially conformal with the outer shell along one or both sides of the analyzer, and form a substantial portion of one or both sides of the analyzer. Longitudinal fins may be placed on an outer face of the heat sink to aid in thermal conduction from the (Continued)

engine to the surrounding air. Thermal handling, shock/vibration isolation, and moisture barriers are provided.

10 Claims, 6 Drawing Sheets

(51) Int. Cl.
    *G01N 23/223*    (2006.01)
    *H05G 1/06*    (2006.01)

(58) Field of Classification Search
    USPC .......................................................... 378/199
    See application file for complete search history.

(56) References Cited

U.S. PATENT DOCUMENTS

| | | | |
|---|---|---|---|
| 2008/0095319 A1* | 4/2008 | Grodzins | G21K 1/06 378/147 |
| 2009/0225948 A1 | 9/2009 | Burdett, Jr. et al. | |
| 2010/0080351 A1* | 4/2010 | Hession-Kunz | G01N 23/223 378/45 |

\* cited by examiner

PORTABLE X-RAY ANALYZER HAVING VIBRATION, THERMAL AND/OR MOISTURE ISOLATION FROM EXTERIOR ENVIRONMENT

CROSS-REFERENCE TO RELATED APPLICATIONS

This application is a national stage filing under section 371 of International Application No. PCT/US2013/027918, filed on Feb. 27, 2013, and published on Sep. 6, 2013 as WO 2013/130531 A1. In addition, this application claims the benefit of U.S. provisional patent application Ser. No. 61/604,933, filed Feb. 29, 2012. Each of these application are hereby incorporated herein by reference in its entirety.

TECHNICAL FIELD

The present invention relates to environment isolation apparatus for a portable x-ray analyzer, including vibration, thermal and/or moisture isolation.

BACKGROUND OF THE INVENTION

X-ray analysis of samples is a growing area of interest across many industries such as medical, pharmaceutical, and petroleum. Moving analysis from the laboratory to the field is becoming increasing popular for many reasons, including reduction in size and costs of analyzer components, as well as industry's continually increasing needs for better and faster data collection in areas remote from a laboratory (e.g., production lines, store shelves, raw material sites, mobile compliance vans, transportation and customs hubs, etc.). Moving sensitive instruments to these areas presents certain challenges, including shielding, sample presentation, vibration damping, thermal handling, and moisture barriers, for which unique resolutions are in continuing demand.

SUMMARY OF THE INVENTION

The shortcomings of the prior art are overcome and additional advantages are provided by the present invention which in one aspect is a handheld x-ray analyzer, having an outer shell forming an inner cavity, the outer shell having at least one aperture; an x-ray engine positioned within the cavity; and a generally planar heat sink rigidly and thermally attached to the x-ray engine, and positioned in the aperture of the outer shell thereby substantially filling the aperture while providing thermal conduction between the engine and surrounding air.

An outer face of the heat sink may be substantially conformal with the outer shell along one or both sides of the analyzer, and form a substantial portion of one or both sides of the analyzer. Longitudinal fins may be placed on an outer face of the heat sink to aid in thermal conduction from the engine to the surrounding air.

A flexible material may be placed between an outer perimeter of the heat sink and an edge of the aperture of the outer shell, thereby providing mechanical isolation between the heat sink and the outer shell; and the engine may be mounted within the cavity using a flexible connection between the engine and an inner surface of the outer shell, thereby providing mechanical isolation therebetween.

The x-ray engine may include at least one x-ray optic, an x-ray source, and a power supply for the x-ray source, which are generally mechanically and thermally isolated from the outer shell, thereby maintaining alignment between each other and a focal area of the analyzer.

A flexible barrier material may be placed between an outer perimeter of the heat sink and an edge of the aperture of outer shell; and the engine may be mounted within the cavity using a flexible barrier material entirely around the engine and an inner surface of the outer shell; thereby providing moisture isolation between the between at least portions of the engine and the surrounding environment of the analyzer.

Further additional features and advantages are realized through the techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in connection with the accompanying drawings in which:

DETAILED DESCRIPTION OF THE INVENTION

As discussed above, handheld x-ray analyzers have gained in popularity over the last few years because of their transportability and ease of use. However, the transport and use of these analyzers, as well as more advanced x-ray engines of the type discussed herein, in various operational environments presents challenges in the areas of thermal handling, vibration damping, and moisture barriers.

Figure 1:
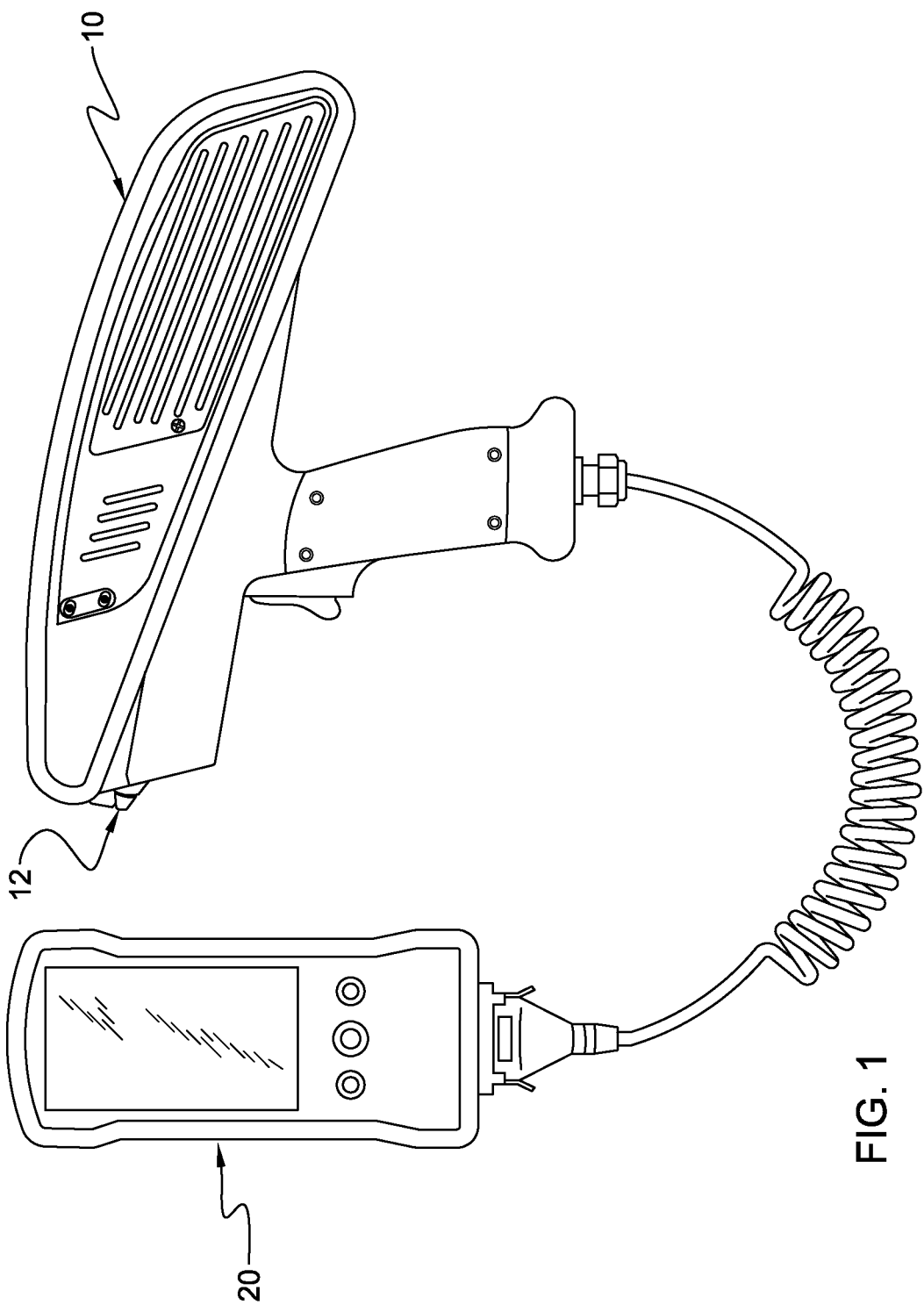
FIG. 1 is a perspective view of an exemplary handheld x-ray analysis instrument and related human interface module.

In accordance with the present invention, and with reference to FIG. 1, a handheld x-ray analyzer 10 includes a sample aperture 12 which transmits excitation x-rays and against which a sample is typically placed. Also shown in FIG. 1 is a human interface module 20, which may include the user interface and/or a power source for the handheld analyzer 10. Such an interface may also be integral to the analyzer 10.

Figure 2:
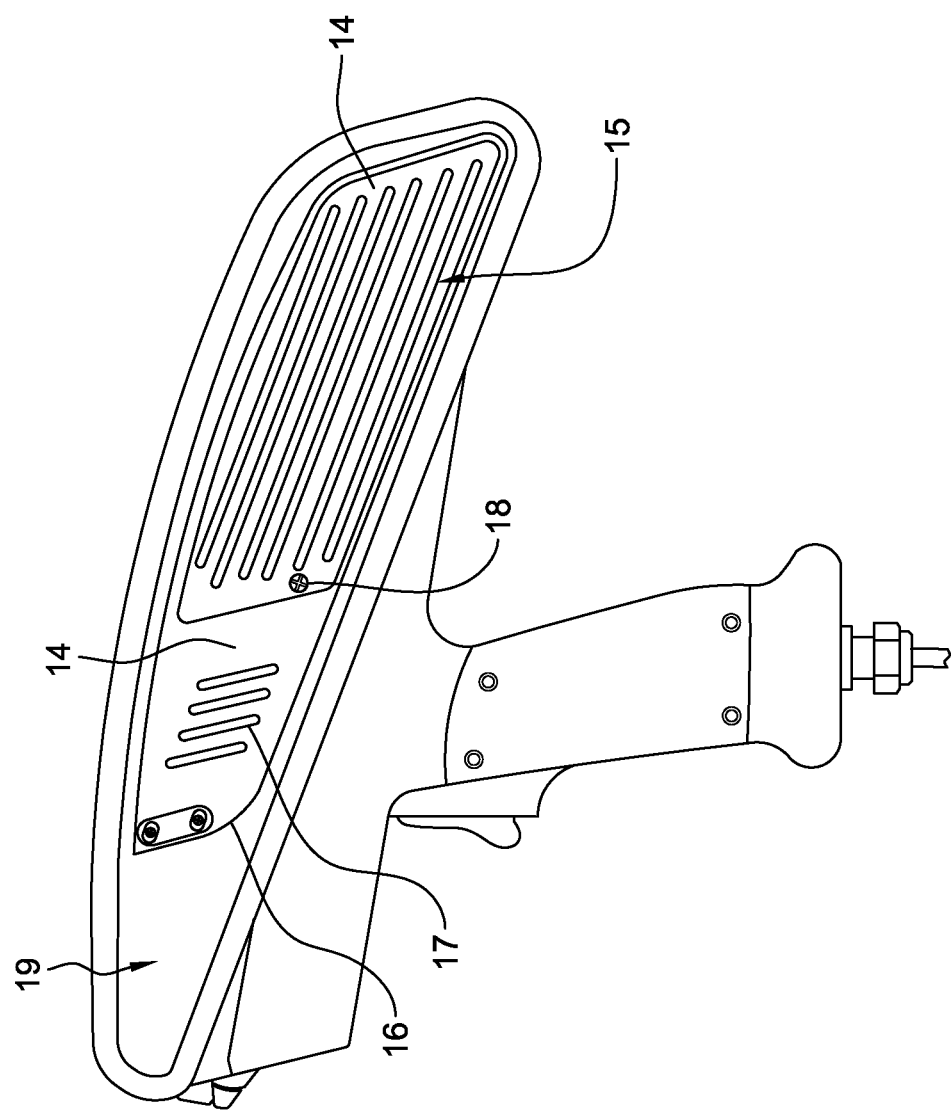
FIG. 2 is an enlarged side view of the analyzer showing the heat sink area of the outer shell.
Figure 3:
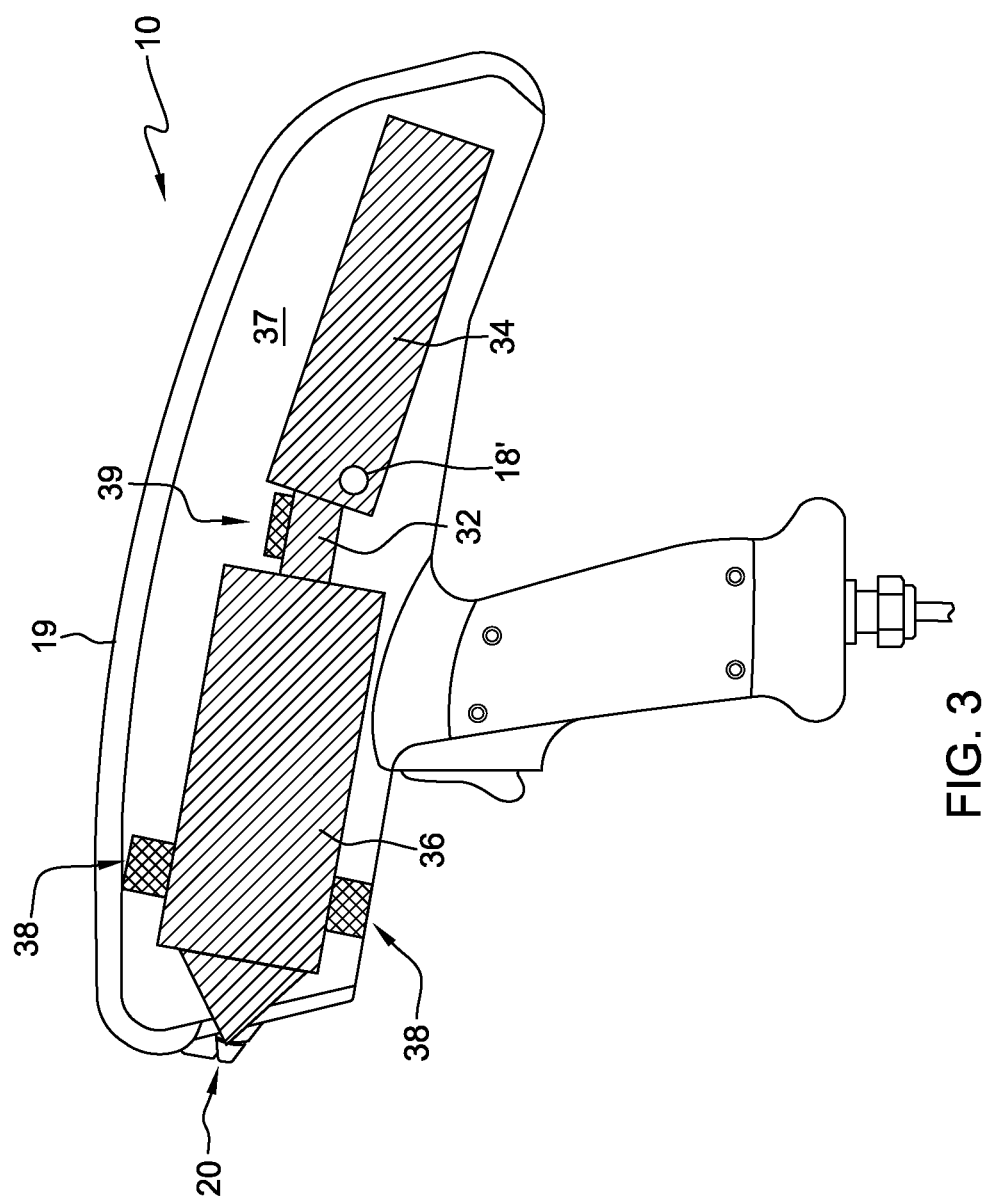
FIG. 3 is an enlarged, partially cutout view of the analyzer showing interior components thereof.
Figure 4:
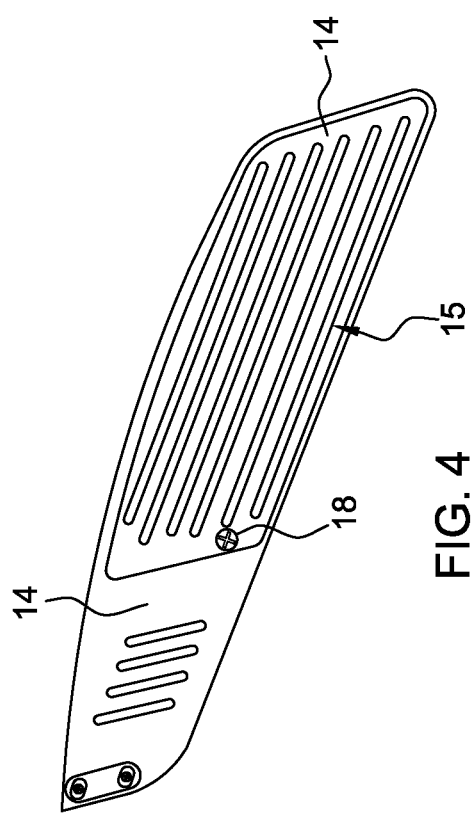
FIG. 4 is an enlarged view of the heat sink of the present invention.

In accordance with the present invention, and with reference to the enlarged side view of FIGS. 2-4, heat sink 14 is disclosed forming a significant part of the side surface of the analyzer, is positioned within an aperture of outer shell 19, and may be generally planar in profile, and formed from a thermally conductive material, e.g., aluminum. Heat sink 14 includes multiple features in accordance with the present invention including but not limited to: longitudinal fins 15 embedded into the outer face of the heat sink for heat dissipation from interior components of the analyzer into the outer environment; pass through holes 17 for e.g., status indicator lights or other indicia; mounting holes/screws 18 for rigid mounting to interior, heat generating components; and perimeter 16—to which a soft, gasketed connection can be made to analyzer outer shell 19.

With reference to the cutaway view of FIG. 3, exemplary interior analyzer components are shown forming an exemplary x-ray "engine," including x-ray source 32, high voltage power supply 34 which powers the x-ray source; x-ray optic assembly 36 which holds 1 or more x-ray optics (discussed further below) and which guides x-rays toward aperture 20 for illumination of a sample.

Thermal Management:

In accordance with the present invention, major heat-generating components including x-ray source 32 and power supply 34 can be rigidly, thermally connected together, and to heat sink 14, via direct attachment thereto using screw/hole 18/18' or other mounting techniques. This provides a direct, thermal connection from these interior components to the exterior environment via heat sink, which can be formed from a heat conductive material, such as aluminum. Also, based on the "floating" of these components within shell 19 (discussed further below), these components are substantially not in contact with outer shell 19 and therefore additional air circulation (and mechanical isolation) is provided in spaces 37, aided by an optional fan 39.

Shock/Vibration Management:

In accordance with the present invention, the major interior components are substantially not in contact with outer shell 19, but rather "float" within the shell 19, held in place primarily by flexible material, such as polyurethane foam (e.g., poron) or springs 38 placed at various points which flexibly hold these "engine" components (32, 34 and/or 36) in place, while providing shock/vibration damping between the rigid outer shell 19 and the engine components. In addition, as discussed above, heat sink 14 may also be rigidly and thermally connected to the interior engine components. To provide shock/vibration isolation between heat sink 14 and shell 19, a flexible material such as foam tape (e.g., silicon foam) can be used between the perimeter 16 of the heat sink and surrounding shell areas (between e.g., mating flanges). This prevents a rigid connection between the heat sink and the remainder of shell 19. Because most impact is expected to be on the shell 19 (from dropping etc on the top, bottom, front or rear), this flexible connection between the side heat sink and shell 19 will prevent transmission of any shock to shell 19 toward the sensitive interior engine components discussed above.

Moisture Management:

In accordance with the present invention, the flexible material 38 may surround assembly 36, thereby providing a moisture barrier between the forward areas of the analyzer, and the more sensitive areas toward the rear. The foam tape between heat sink 14 and shell 19 can also provide a moisture barrier function.

Notably, though the left side of the analyzer is shown above, any or all of the features above (especially heat sink 14) can be implemented on the opposite, right side of the analyzer (not shown). In addition, shell 19 can be formed in two halves (left and right) which can mate using a tongue-in-groove technique, providing an additional moisture barrier.

The handheld x-ray analyzers useable with the present invention include virtually any portable instruments which would benefit from the advantages provided by the present invention. The x-ray-optic-enabled engines discussed above are of particular interest, and could benefit from the present invention, because of their need for reliability (i.e., they are sensitive to environment) and also because they perform optimally when the sample is highly aligned to the input and/or out focal areas of x-ray optics, which themselves must be aligned to the x-ray source. The following are two examples of x-ray-optic-enabled analyzer engines which may be used in connection with the present invention, and which require a high degree of environmental isolation as discussed above.

Exemplary ME EDXRF X-Ray Analysis Engine:

Monochromatic excitation, energy dispersive x-ray fluorescence (ME-EDXRF) analyzers can be used for this application, in accordance with the present invention. Various aspects of this package have been disclosed in the commonly assigned, previously-filed U.S. Provisional Applications entitled X-RAY OPTIC AND SOURCE ASSEMBLY FOR PRECISION X-RAY ANALYSIS APPLICATIONS, filed Mar. 5, 2008 as Ser. No. 61/033,899; and HIGHLY ALIGNED X-RAY OPTIC AND SOURCE ASSEMBLY FOR PRECISION X-RAY ANALYSIS APPLICATIONS, filed Mar. 25, 2008 as Ser. No. 61/039,220 now U.S. Pat. No. 7,738,630 B2; and XRF SYSTEM HAVING MULTIPLE EXCITATION ENERGY BANDS IN HIGHLY ALIGNED PACKAGE, filed Apr. 7, 2008, as Ser. No. 61/042,974 now U.S. Patent Publication No. 2011/0170666 A1, published Jul. 14, 2011; previously filed PCT Application entitled XRF SYSTEM HAVING MULTIPLE EXCITATION ENERGY BANDS IN HIGHLY ALIGNED PACKAGE, filed Mar. 3, 2009 as serial no. PCT/US2009/035847; and SUPPORT STRUCTURE FOR MULTIPLE HIGHLY ALIGNED X-RAY OPTICS filed Oct. 26, 2011 as Ser. No. 61/551,602; each of which is assigned to X-Ray Optical Systems, Inc., the assignee of the present invention, and each of which is hereby incorporated herein by reference in its entirety.

Figure 5:
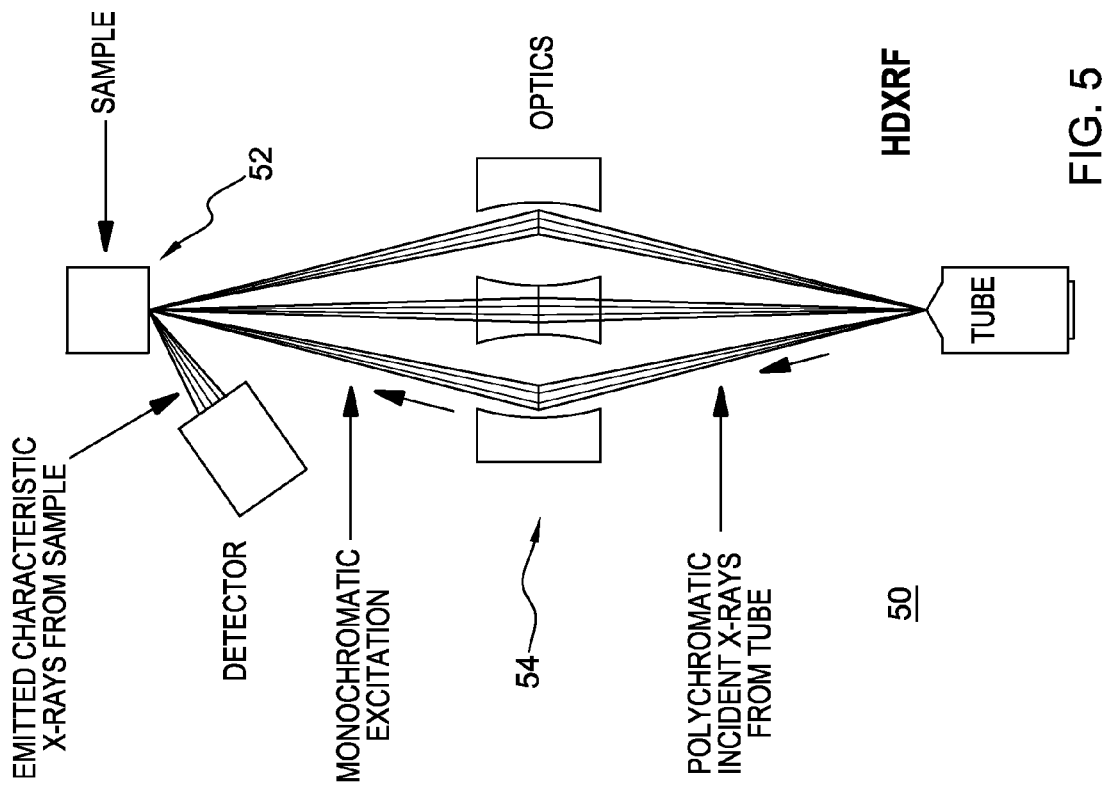
FIG. 5 is a schematic view of an exemplary ME EDXRF x-ray engine useable with the transport apparatus of the present invention.

In one embodiment this engine 50 involves monochromatic excitation known as HD XRF as depicted schematically in FIG. 5. HD XRF is a multi-element analysis technique offering significantly enhanced detection performance over traditional ED or WD XRF. This technique applies state-of-the-art monochromating and focusing optics 54 illuminating a focal area 52, enabling multiple select-energy excitation beams that efficiently excite a broad range of target elements in the sample. Monochromatic excitation dramatically reduces scattering background under the fluorescence peaks, greatly enhancing elemental detection limits and precision. HDXRF is a direct measurement technique and does not require consumables or special sample preparation.

Exemplary MWD XRF X-Ray Analysis Engines:

XOS has previously disclosed a Monochromatic Wavelength Dispersive X-ray Fluorescence (MWDXRF) analyzer using two monochromating optic sets (U.S. Pat. Nos. 6,934,359 and 7,072,439—hereby incorporated by reference herein in their entirety), as shown schematically in FIG. 6. The related SINDIE (Sulfur IN DIEsel) product line for the measurement of sulfur in diesel fuel and other fuel distillates revolutionized XRF and provides many advantages including: (1) signal/background (S/B) is improved due to monochromatic excitation of the sample by DCC1, i.e., the bremsstrahlung photons with energies under fluorescence peaks (which normally swamp these peaks of interest) can only reach the detector through scattering, therefore improving the S/B ratio dramatically compared to polychromatic excitation; (2) superior energy resolution—this eliminates all common interference problems and provides the physical basis for upstream applications; (3) inherent robustness and low maintenance—the analysis engine is low power, compact, with no moving parts or consumable gasses; and (4) unprecedented dynamic range, e.g., a quantification level from 0.3 ppm to 5% of sulfur in a sample.

Figure 6:
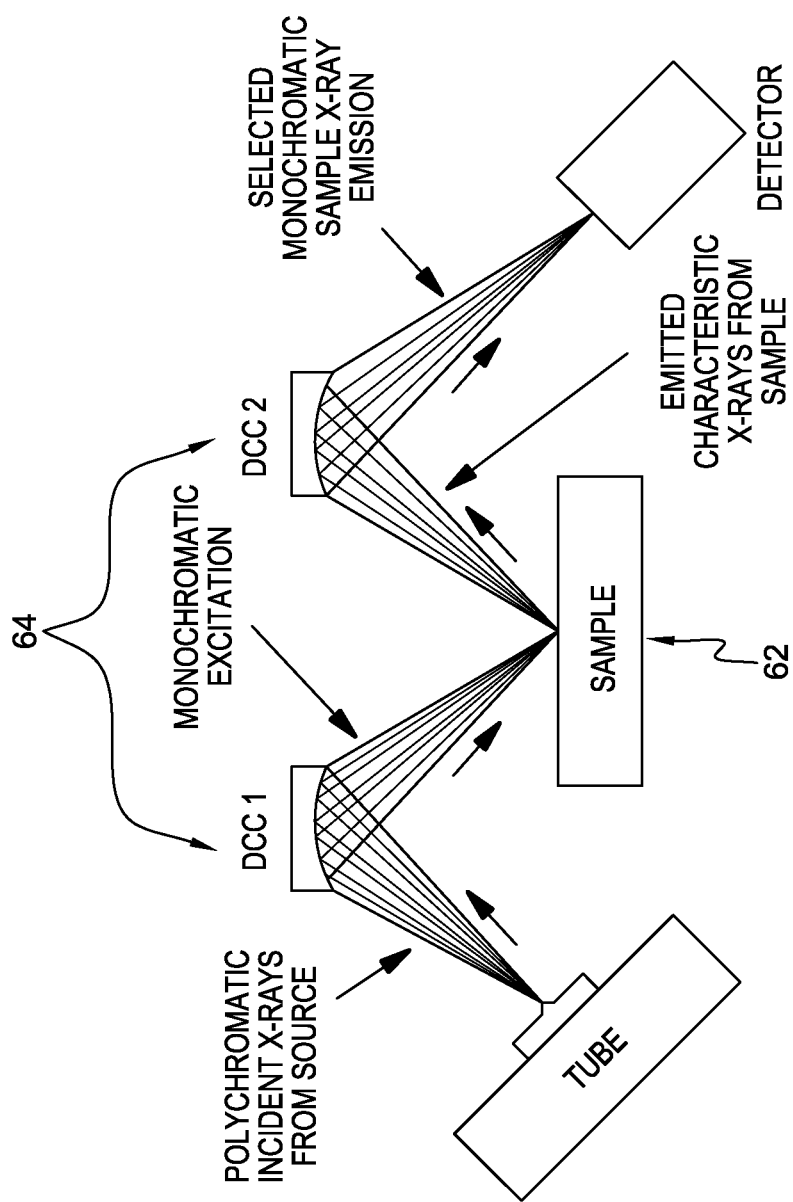
FIG. 6 a schematic view of an exemplary MWD XRF x-ray engine useable with the transport apparatus of the present invention.

The MWD XRF engine 60, shown schematically in FIG. 6, includes curved monochromating optics 64 in the excitation and detection paths, forming focal area 62, which is the configuration of the SINDIE sulfur analyzer discussed above. However, an optic may only be present in one of these paths, which still requires precise alignment. In one example, an optic of any of the above-described types may only be present in the excitation path, and the detection path would include an energy dispersive detector. This is the common configuration of an energy dispersive x-ray fluorescence (EDXRF) system.

Optics for advanced XRF systems, including those below, may include, for example, curved crystal monochromating optics such as those disclosed in commonly assigned U.S. Pat. Nos. 6,285,506; 6,317,483; and 7,035,374; and/or multilayer optics such as those disclosed in commonly assigned U.S. Patent Application entitled "X-Ray Focusing Optic Having Multiple Layers With Respective Crystal Orientations," U.S. Ser. No. 11/941,377 filed Nov. 16, 2007; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506 and 7,209,545 are also useable. Each of the above-noted patents and patent applications is incorporated herein by reference in its entirety.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A handheld x-ray analyzer, comprising:
   an outer shell forming an inner cavity, the outer shell having at least one aperture;
   an x-ray engine positioned within the cavity;
   a generally planar heat sink rigidly and thermally attached to at least one heat generating component of the x-ray engine, and positioned in the aperture of the outer shell thereby substantially filling the aperture while providing thermal conduction between the engine and surrounding air.

2. The analyzer of claim 1, wherein an outer face of the heat sink is substantially conformal with the outer shell along one or both sides of the analyzer.

3. The analyzer of claim 2, wherein the outer face of the heat sink forms a substantial portion of one or both sides of the analyzer.

4. The analyzer of claim 1, further comprising longitudinal fins on an outer face of the heat sink to aid in thermal conduction from the engine to the surrounding air.

5. The analyzer of claim 1, comprising a flexible material placed between an outer perimeter of the heat sink and an edge of the aperture of the outer shell, thereby providing mechanical isolation between the heat sink and the outer shell.

6. The analyzer of claim 1, wherein the engine is mounted within the cavity using a flexible connection between the engine and an inner surface of the outer shell, thereby providing mechanical isolation therebetween.

7. The analyzer of claim 6, wherein the x-ray engine comprises at least one x-ray optic, an x-ray source, and a power supply for the x-ray source, which are generally mechanically and thermally isolated from the outer shell, thereby maintaining alignment between each other and a focal area of the analyzer.

8. The analyzer of claim 7, wherein the at least one x-ray optic comprises a curved monochromating optic or a polycapillary optic.

9. The analyzer of claim 7, wherein the x-ray engine comprises an EDXRF or MWDXRF x-ray excitation engine.

10. The analyzer of claim 1, further comprising:
    a flexible barrier material placed between an outer perimeter of the heat sink and an edge of the aperture of outer shell; and
    wherein the engine is mounted within the cavity using a flexible barrier material entirely around the engine and an inner surface of the outer shell;
thereby providing moisture isolation between the between at least portions of the engine and the surrounding environment of the analyzer.

* * * * *